US012663320B2

(12) United States Patent
Maruyama et al.

(10) Patent No.: US 12,663,320 B2
(45) Date of Patent: Jun. 23, 2026

(54) TEMPERATURE MEASUREMENT DEVICE, THERMOMETER, TEMPERATURE MEASUREMENT METHOD, AND TEMPERATURE ATTENUATION MEASUREMENT METHOD

(71) Applicants:SEMITEC Corporation, Tokyo (JP); National Institute of Technology, Tokyo (JP); HIROSAKI UNIVERSITY, Aomori (JP)

(72) Inventors: Shigenao Maruyama, Aomori (JP); Yuya Iseki, Aomori (JP); Takuma Kogawa, Aomori (JP); Takashi Nonaka, Aomori (JP); Yasushi Hosokawa, Aomori (JP); Takahiro Okabe, Aomori (JP); Yutaro Tabata, Tokyo (JP); Tadashi Matsudate, Tokyo (JP); Toshinori Nakajima, Tokyo (JP); Masaya Higashi, Tokyo (JP); Manabu Orito, Tokyo (JP)

(73) Assignees: SEMITEC Corporation, Tokyo (JP); National Institute of Technology, Tokyo (JP); HIROSAKI UNIVERSITY, Aomori (JP)

( * ) Notice: Subject to any disclaimer, the term of this patent is extended or adjusted under 35 U.S.C. 154(b) by 427 days.

(21) Appl. No.: 18/267,772

(22) PCT Filed: Jan. 12, 2022

(86) PCT No.: PCT/JP2022/000656
§ 371 (c)(1),
(2) Date: Jun. 15, 2023

(87) PCT Pub. No.: WO2022/158343
PCT Pub. Date: Jul. 28, 2022

(65) Prior Publication Data
US 2024/0068884 A1      Feb. 29, 2024

(30) Foreign Application Priority Data
Jan. 19, 2021      (JP) .................................. 2021-006457

(51) Int. Cl.
*G01K 7/22* (2006.01)
*A61B 5/01* (2006.01)
(Continued)

(52) U.S. Cl.
CPC .................. *G01K 7/22* (2013.01); *A61B 5/01* (2013.01); *G01K 1/16* (2013.01); *G01K 7/42* (2013.01); *G01K 13/20* (2021.01); *A61B 5/444* (2013.01)

(58) Field of Classification Search
CPC .. G01K 7/22; G01K 1/16; G01K 7/42; G01K 13/20; A61B 5/01; A61B 5/444
See application file for complete search history.

(56) References Cited

U.S. PATENT DOCUMENTS 4,937,552 A * 6/1990 Lam .......................... G01K 7/18
374/E1.022
5,112,136 A * 5/1992 Sakuma ................. G01N 25/18
374/110
(Continued)

FOREIGN PATENT DOCUMENTS

CN        102106724        6/2011
CN        102466526        5/2012
(Continued)

OTHER PUBLICATIONS

"International Search Report (Form PCT/ISA/210) of PCT/JP2022/000656", mailed on Apr. 5, 2022, with English translation thereof, pp. 1-4.
(Continued)

*Primary Examiner* — Laura Martin
*Assistant Examiner* — Philip L Cotey
(74) *Attorney, Agent, or Firm* — JCIPRNET

(57) ABSTRACT
A thermosensitive part sensing temperature; a temperature sensor for measurement provided in the unit and measuring temperature by contacting the unit with a body to be measured; a temperature detecting part detecting, from when the unit contacts the body, the time when the sensor senses a difference from an initial temperature of the sensor, and a measured temperature of the sensor at that time, and detecting, from when the difference is sensed, a time after a certain length of time and a measured temperature of the sensor at
(Continued)

that time; an estimating part estimating, from the time when the difference is sensed and a time after a certain length of time, the time when the thermosensitive part contacts the body, and the measured temperature at that time; and a heat conduction analyzing part estimating the measured temperature based on output information from the temperature detecting part and the estimating part.

20 Claims, 9 Drawing Sheets

(51) Int. Cl.

| | | |
|---|---|---|
| *G01K 1/16* | (2006.01) |
| *G01K 7/42* | (2006.01) |
| *G01K 13/20* | (2021.01) |
| *A61B 5/00* | (2006.01) |

(56) References Cited

U.S. PATENT DOCUMENTS

| | | | | |
|---|---|---|---|---|
| 2006/0224349 | A1* | 10/2006 | Butterfield | G01K 7/42 |
| | | | | 374/E7.042 |
| 2012/0114011 | A1* | 5/2012 | Rose | G01K 7/16 |
| | | | | 374/E7.018 |
| 2014/0114143 | A1* | 4/2014 | Sano | A61B 5/4812 |
| | | | | 600/301 |
| 2014/0278201 | A1* | 9/2014 | Shimizu | G01K 7/427 |
| | | | | 702/131 |
| 2021/0199514 | A1* | 7/2021 | Shimuta | G01K 7/42 |
| 2022/0125388 | A1* | 4/2022 | Buller | A61B 5/0008 |
| 2022/0128413 | A1* | 4/2022 | Smits | G01K 1/165 |
| 2022/0196483 | A1* | 6/2022 | Kobayashi | B60L 3/00 |

FOREIGN PATENT DOCUMENTS

| | | |
|---|---|---|
| CN | 109540961 | 3/2019 |
| JP | H07111383 | 11/1995 |
| JP | H1183630 | 3/1999 |
| JP | 2001218742 | 8/2001 |
| JP | 3558397 | 8/2004 |
| JP | 2004531741 | 10/2004 |
| JP | 3920662 | 5/2007 |
| JP | 4949648 | 6/2012 |
| JP | 2013210356 | 10/2013 |
| JP | 2014174084 | 9/2014 |
| JP | 2016217885 | 12/2016 |
| JP | 2019507322 | 3/2019 |
| WO | 2004094970 | 11/2004 |

OTHER PUBLICATIONS

"The First Office Action of China Counterpart Application", issued on Mar. 25, 2026, with English translation thereof, p. 1-p. 13.

\* cited by examiner (a)

Temperature attenuation measurement
Operation of sensor

| Step | Time t[s] | Operation |
|---|---|---|
| 1 | t<2 | Temperature monitoring |
| 2 | 2≦t≦2.1 | Sensor 1 : applied short pulse (3mJ)<br>Sensor 2 : follow sensor 1 |
| 3 | 2.1<t<4 | Temperature monitoring |
| 4 | 4≦t≦7 | Sensor 1 : applied long pulse (3mJ)<br>Sensor 2 : follow sensor 1 |
| 5 | 7<t<15 | Temperature monitoring |

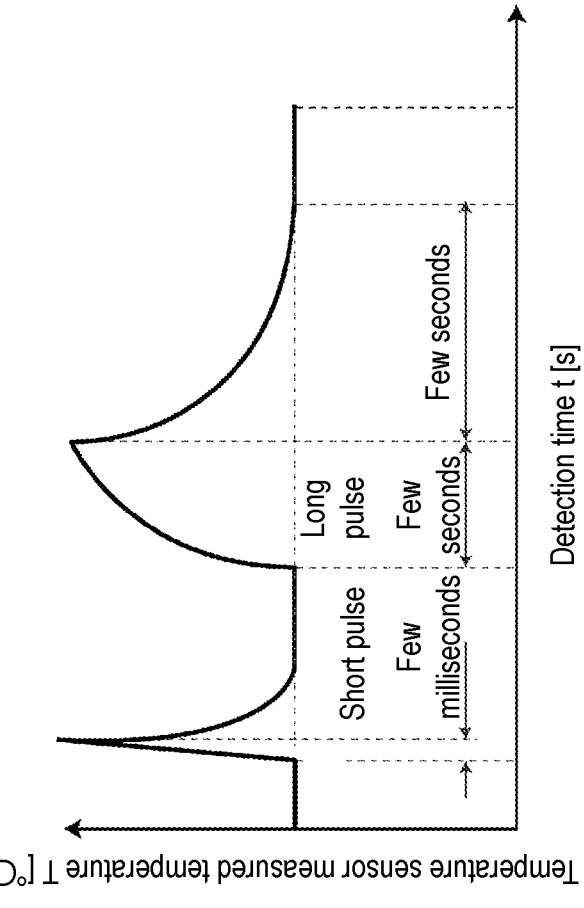

Temperature sensor measured temperature T [°C]

Short pulse
Few
milliseconds

Long
pulse
Few
seconds

Few seconds

Detection time t [s]

FIG. 13

TEMPERATURE MEASUREMENT DEVICE, THERMOMETER, TEMPERATURE MEASUREMENT METHOD, AND TEMPERATURE ATTENUATION MEASUREMENT METHOD

CROSS-REFERENCE TO RELATED APPLICATION

This application is a 371 application of the International PCT application serial no. PCT/JP2022/000656, filed on Jan. 12, 2022, which claims the priority benefits of Japan Patent Application No. 2021-006457, filed on Jan. 19, 2021. The entirety of each of the above-mentioned patent applications is hereby incorporated by reference herein and made a part of this specification.

TECHNICAL FIELD

This invention relates to a temperature measurement device, a thermometer, a temperature measurement method, and a temperature attenuation measurement method.

RELATED ART

Conventionally, in the industrial and medical fields, it is desirable to measure the surface temperature of objects with high precision, high accuracy, and high-speed response.

For example, electronic thermometers for general household use, which measure the body temperature of a living body as a body to be measured, are in widespread use. In such electronic thermometers, the measurement time for body temperature, when measured under the armpit, requires approximately 10 minutes in actual measurement methods.

Furthermore, there is an electronic thermometer called predictive electronic thermometer. This predictive electronic thermometer predicts the equilibrium temperature at which the temperature rise stops and displays the temperature, making measurement possible in about 1 to 2 minutes. Various configurations and methods have been proposed to shorten the measuring time like this.

CITATION LIST

Patent Literature

[Patent Literature 1] Japanese Patent Publication No. 7-111383
[Patent Literature 2] Japanese Patent No. 3558397
[Patent Literature 3] Japanese Patent No. 3920662
[Patent Literature 4] Japanese Patent No. 4949648
[Patent Literature 5] Japanese Unexamined Patent Application Publication No. 2016-217885

SUMMARY OF INVENTION

Technical Problem

However, even if the time is short, spending time on measurement may often be bothersome and burdensome for the measurer.

An embodiment of the present invention us is to provide provides a temperature measurement device, thermometer, temperature measuring method, and temperature attenuation measuring method capable of realizing high-speed response and measuring the temperature of a body to be measured in a short time with high precision and high accuracy.

Moreover, it also provides an effective method for diagnosing skin cancer and the like in living organisms, for example.

Solution to Problem

The temperature measurement device according to an embodiment of the present invention includes a thermosensitive part that senses temperature; a temperature sensor for measurement which is provided in the thermosensitive part and which is capable of measuring temperature by bringing the thermosensitive part into contact with a body to be measured; a temperature detecting part for detecting, from when the thermosensitive part is brought into contact with the body to be measured, a time when the temperature sensor for measurement senses a difference from an initial temperature of the temperature sensor for measurement and a measured temperature of the temperature sensor for measurement at that time, and for detecting, from when the difference is sensed, a time after a certain length of time and a measured temperature of the temperature sensor for measurement at that time; an estimating part for estimating, from the time when the difference is sensed and the time after the certain length of time and the measured temperatures at that times, a time when the thermosensitive part comes into contact with the body to be measured; and a heat conduction analyzing part for estimating a measured temperature based on an output information of the temperature detecting part and estimating part. Such a temperature measurement device may be suitably used for a thermometer.

With the temperature measurement device of the present embodiment, it is possible to achieve high-speed response, and the temperature of the body to be measured can be measured in a short time with high precision and high accuracy. Although the temperature measurement device is suitably applied to living organisms, the present invention is not limited to thereto. It may also be applied to measure the surface temperature of objects in industrial fields, and the body to be measured is not particularly limited.

The temperature measurement method according to the embodiment of the present invention includes a thermosensitive part that senses temperature, and a temperature sensor for measurement which is provided in the thermosensitive part and which is capable of measuring temperature by bringing the thermosensitive part into contact with a body to be measured. The method includes a first detection step for detecting, from when the thermosensitive part is brought into contact with the body to be measured, a time when the temperature sensor for measurement senses a difference from an initial temperature of the temperature sensor for measurement and a measured temperature of the temperature sensor for measurement at that time; a second detection step for detecting, from when the difference is sensed, a time after a certain length of time and a measured temperature of the temperature sensor for measurement at that time; a contact time estimating step for estimating, based on the time when the difference is sensed and the time after the certain length of time, and the measured temperatures at the times, a time when the thermosensitive part comes into contact the body to be measured; and a temperature estimation step for estimating, from the times and the measured temperatures detected in the first detection step and the second detection step and the time estimated in the contact time estimation step, a temperature of the body to be measured by unsteady heat conduction analysis.

Furthermore, the temperature measurement method according to the embodiment of the present invention includes a thermosensitive part that senses temperature, and a temperature sensor for measurement which is provided in the thermosensitive part and which is capable of measuring temperature by bringing the thermosensitive part into contact with a body to be measured. The method estimates the temperature of the body to be measured by unsteady heat conduction analysis, then heating the temperature sensor for measurement to at least the temperature estimated, and measures the temperature of the body to be measured, with the thermosensitive part and the body to be measured in a thermal equilibrium state.

By using such a temperature measurement method according to the embodiment, it is possible to measure the temperature of the body to be measured in a short time.

Furthermore, the temperature attenuation measurement method according to the embodiment of the present invention includes a step of bringing a thermosensitive part into contact with a body to be measured; a step of applying a constant power first heat pulse to a temperature sensor for measurement; a step of detecting the temperature attenuation characteristics of the temperature sensor for measurement after a certain length of time from stopping the application of the first heat pulse; a step of applying a constant power second heat pulse, having a longer time width than the first heat pulse, to the temperature sensor for measurement; and a step of detecting the temperature attenuation characteristics of the temperature sensor for measurement after a certain length of time from stopping the application of the second heat pulse.

According to the temperature attenuation measurement method of the present embodiment, for example, by detecting the temperature attenuation characteristics from the epidermis of a living body to the dermis and calculating the thermal conductivity, it is possible to diagnose affected areas non-invasively.

Effects of Invention

According to an embodiment of the present invention, it is possible to provide a temperature measuring device, a clinical thermometer, a temperature measuring method, and a temperature attenuation measuring method capable of realizing even higher-speed response and measuring the temperature of a body to be measured in a short time with high precision and high accuracy.

BRIEF DESCRIPTION OF DRAWINGS

FIG. 12 is an explanatory diagram showing the operation of a temperature sensor in temperature measurement.

FIG. 13 is an explanatory diagram showing the operation of a temperature sensor in temperature attenuation measurement.

DESCRIPTION OF EMBODIMENTS

Figure 1:
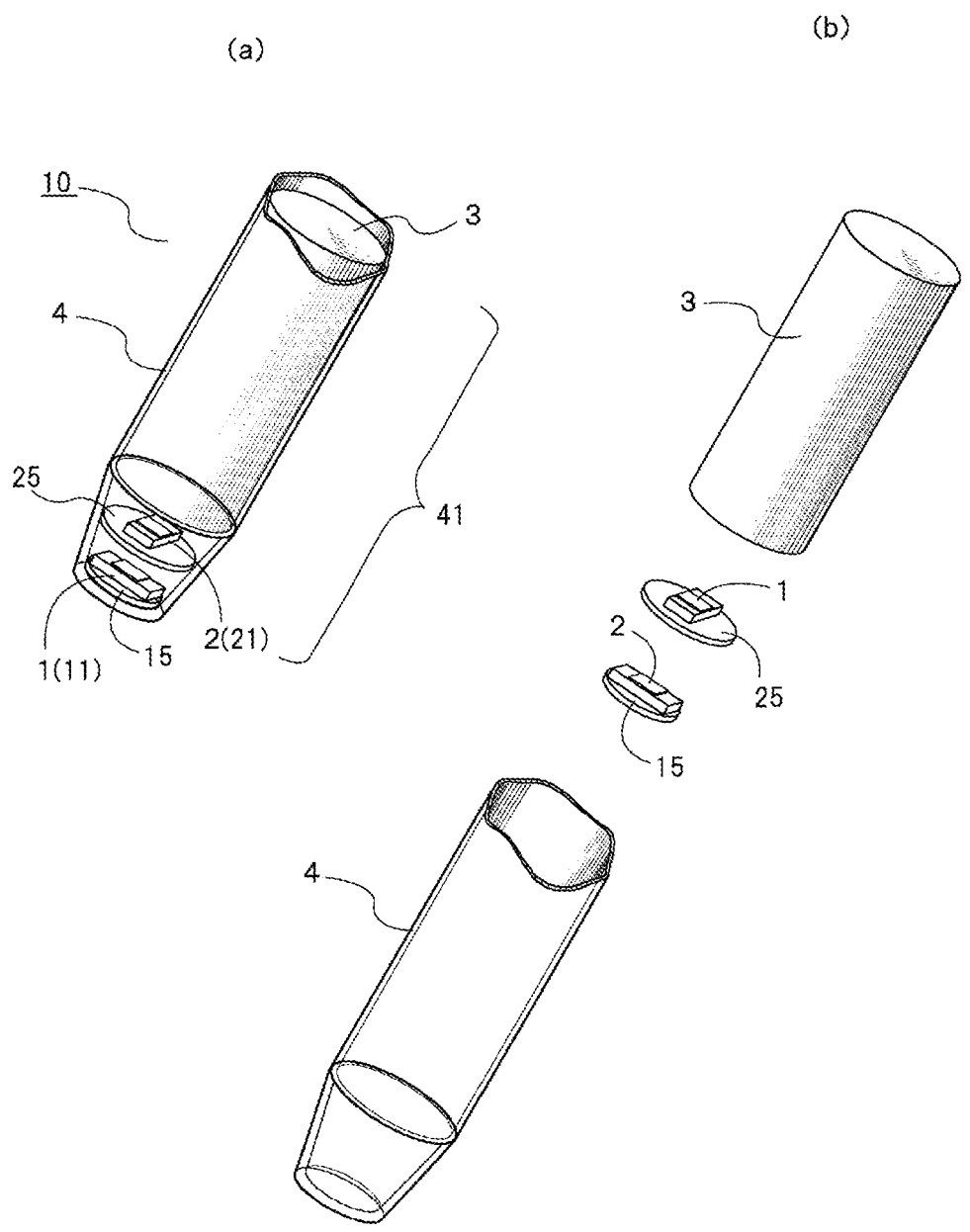
FIG. 1 shows main parts of a temperature measurement device according to the embodiment of the present invention, where (a) is an oblique view, and (b) is an exploded oblique view.
Figure 2:
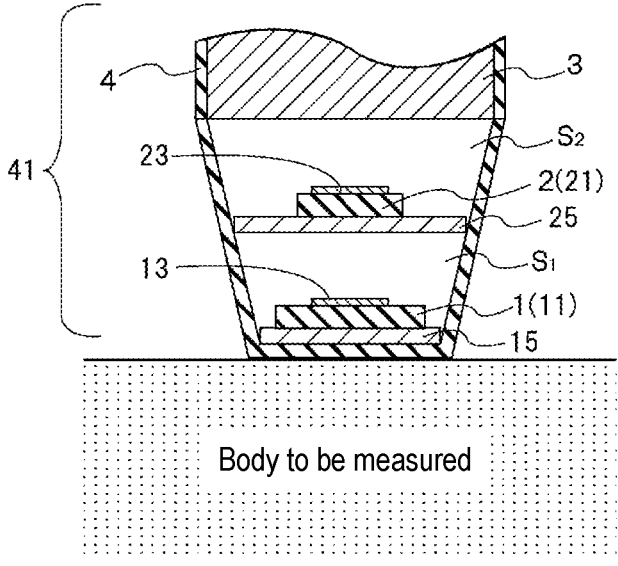
FIG. 2 is a cross-sectional view showing main parts of the temperature measurement device.
Figure 3:
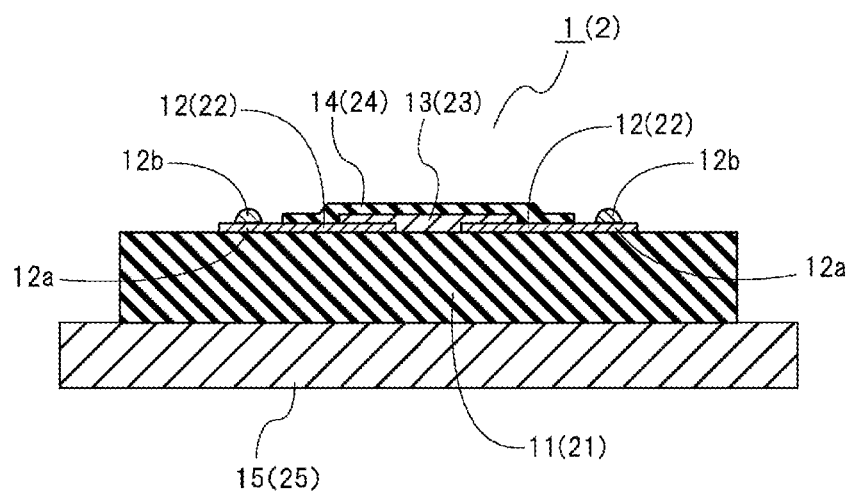
FIG. 3 is a cross-sectional view showing a temperature sensor.
Figure 4:
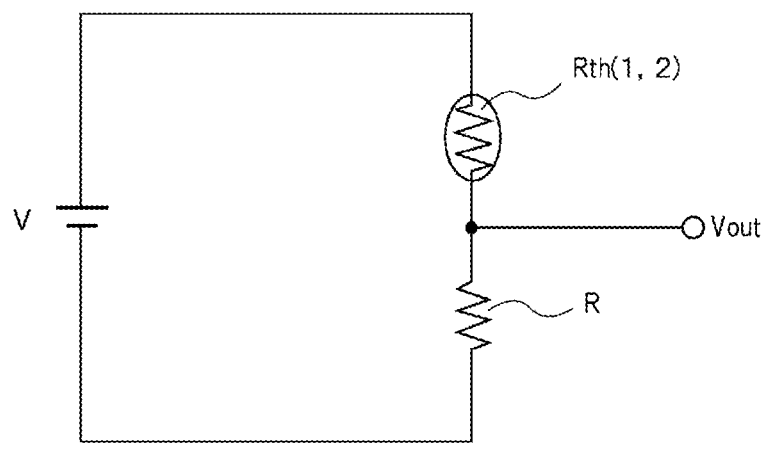
FIG. 4 is a wiring diagram showing a basic connection state of a temperature sensor.
Figure 5:
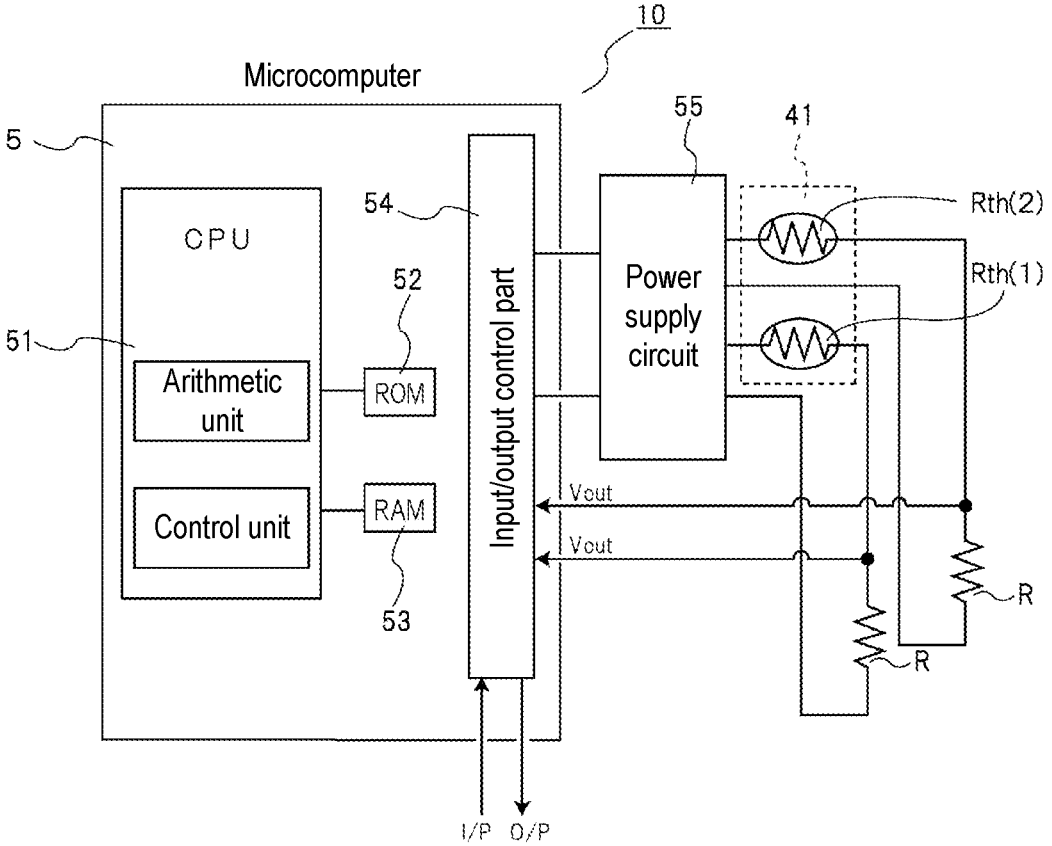
FIG. 5 is a block configuration diagram showing a temperature measurement device.

Referring to FIGS. 1 to 5, an explanation will be given of a temperature measurement device according to an embodiment of the present invention. FIG. 1 is a schematic perspective view and exploded perspective view showing main parts of a temperature measurement device, and FIG. 2 is a cross-sectional view schematically showing main parts of the temperature measurement device. Further, FIG. 3 is a cross-sectional view showing the temperature sensor, FIG. 4 is a wiring diagram showing a basic connection state of the temperature sensor, and FIG. 5 is a block configuration diagram showing the temperature measurement device. In FIGS. 1 and 2, the illustration of wiring relationships such as lead wires is omitted. In each figure, the scale of each member may be appropriately changed in order to make each member recognizable in size. Also, the same or equivalent parts are denoted by the same reference numerals, and redundant descriptions are omitted.

As shown in FIGS. 1 and 2, a temperature measurement device 10 includes a temperature sensor 1 for measurement, a temperature sensor 2 for protective heating, a heat sink 3, a pipe-shaped outer shell 4 in which these components are housed, and a control processing unit (see FIG. 5) for controlling each component.

The temperature sensor 1 for measurement has basically the same specifications and characteristics as the temperature sensor 2 for protective heating, which will be described later. The temperature sensor 1 for measurement is a thin film temperature sensing element and is a thin film thermistor. As shown with reference to FIG. 3, the temperature sensor 1 for measurement includes an element substrate 11, a conductive layer 12 formed on this substrate 11, a thin film element layer 13, and a protective insulating layer 14. Moreover, the temperature sensor 1 for measurement is arranged on an arrangement plate 15 formed of a material with good thermal conductivity, such as aluminum.

The element substrate 11 has a substantially rectangular shape and is formed of an insulating alumina material. The material for forming the substrate 11 may be ceramics such as aluminum nitride, zirconia, or semiconductor materials such as silicon, germanium, etc. An insulating thin film is formed on one surface (upper side in the drawing) of the substrate 11 by a sputtering method. The substrate 11 is extremely thin and has a thickness of 200 μm or less, specifically 50 μm to 200 μm, preferably 150 μm or less.

By using such an ultrathin substrate 11 for a thin film thermistor, it is possible to realize a thermosensitive element having a small heat capacity, high sensitivity, and excellent thermal response.

The conductive layer 12 forms the wiring pattern and is formed on the substrate 11. The conductive layer 12 is formed by depositing a metal thin film using a sputtering method, and the metal material includes noble metals such as platinum (Pt), gold (Au), silver (Ag), palladium (Pd), and their alloys, for example, Ag—Pd alloy, etc. Moreover, at both ends of the substrate 11, a pair of electrode portions 12a, which are integrally connected to the conductive layer 12 and electrically connected to the conductive layer 12, are formed.

The thin film element layer 13 is a thermistor composition and is composed of an oxide semiconductor having a negative temperature coefficient. The thin film element layer 13 is electrically connected to the conductive layer 12 by forming a film on the conductive layer 12 using a sputtering method or the like. It should be noted that the thin film element layer may be composed of an oxide semiconductor having a positive temperature coefficient.

The thin film element layer 13 is composed of, for example, two or more elements selected from transition metal elements such as manganese (Mn), nickel (Ni), cobalt (Co), and iron (Fe). The protective insulating layer 14 is formed so as to cover the thin film element layer 13 and the conductive layer 12. The protective insulating layer 14 is a protective glass layer formed by borosilicate glass.

Furthermore, the electrode portion 12a is joined and electrically connected to a metal lead wire 12b. Specifically, the lead wire 12b is formed from a material with low thermal conductivity, such as constantan or Hastelloy (registered trademark), and its thermal conductivity is preferably 5 W/m·K to 25 W/m·K. These may be connected using solder or other brazing materials, or by laser welding. Moreover, it is preferable that the wire diameter of the lead wire 12b is about $\varphi 20$ μm to $\varphi 100$ μm. By configuring the lead wire 12b in this manner, the heat capacity and heat dissipation of the thermistor due to the lead wire 12b can be reduced, and high sensitivity and improved thermal response can be achieved.

The arrangement plate 15, on which the temperature sensor 1 for measurement is arranged, has a substantially circular shape and is arranged at a tip portion of the outer shell 4. Thus, the temperature sensor 1 for measurement is arranged at the tip portion of the outer shell 4. The arrangement plate 15 is formed of a material such as aluminum with good thermal conductivity, and has a small heat capacity such that heat may be transferred to the temperature sensor 1 for measurement with high-speed thermal response. Specifically, the arrangement plate 15 has a size of $\varphi 0.7$ mm to $\varphi 1.7$ mm and a thickness of 0.08 mm to 0.15 mm, preferably a size of $\varphi 1.2$ mm, and a thickness of about 0.1 mm.

The temperature sensor 2 for protective heating is a thin film temperature sensing element and a thin film thermistor. It is the same element as the temperature sensor 1 for measurement and has the same specifications and characteristics. Thus, the same or equivalent symbols are attached to the same or equivalent parts as the temperature sensor 1 for measurement, and detailed explanations are omitted.

The temperature sensor 2 for protective heating is equipped with an element substrate 21, a conductive layer 22 formed on this substrate 21, a thin film element layer 23, and a protective insulating layer 24.

The temperature sensor 2 for protective heating is arranged on an arrangement plate 25 formed of a material with good thermal conductivity, such as aluminum, in the same manner as the temperature sensor 1 for measurement. The arrangement plate 25 has a substantially circular shape and is arranged at tip portion of the outer shell 4 along an inner diameter of the outer shell 4 that expands in a tapered shape. Thus, the arrangement plate 25 is formed to be larger than the arrangement plate 15 on which the temperature sensor 1 for measurement is arranged, and it may exchange heat with the temperature sensor 1 for measurement through a heat insulation layer $S_1$, and is positioned on the rear end side along the longitudinal direction of the outer shell 4.

Specifically, the arrangement plate 25 has a size of $\varphi 1$ mm to $\varphi 2$ mm, and a thickness is 0.08 mm to 0.15 mm, preferably $\varphi 1.5$ mm, and a thickness of about 0.1 mm.

The heat insulation layer $S_1$ is a gas layer, specifically an air layer, and the thickness of the heat insulation layer $S_1$ is set to a minute interval of 0.05 mm to 1 mm, preferably 0.5 mm. By setting the thickness in this way, the heat from the temperature sensor 1 for measurement is suppressed from being transmitted to the temperature sensor 2 for protective heating, while maintaining an appropriate heat insulating performance, and enabling heat exchange between the temperature sensor 1 for measurement and the temperature sensor 2 for protective heating, making it possible to equalize the temperatures of both.

Moreover, although an air layer is preferable for the heat insulation layer $S_1$, it may be a gas layer of inert gases such as nitrogen or argon, and it may also be composed of heat insulating materials. Furthermore, the thin film element layer 23 of the temperature sensor 2 for protective heating may be arranged to face the temperature sensor 1 for measurement.

At the rear end side of the temperature sensor 2 for protective heating, the heat sink 3 is arranged. The heat sink 3 has a cylindrical shape and is formed by an alumina material that may secure a predetermined thermal conductivity and electrical insulation. The heat sink 3 has a diameter of $\varphi 1.8$ mm and a length of 4.5 mm, and is arranged to fit into the inner diameter of the outer shell 4. It should be noted that it is preferable to place a Peltier element as a temperature control element (not shown) so as to thermally couple with the heat sink 3 on the rear end surface of the heat sink 3. In this case, by keeping the heat sink 3 at a constant low temperature, the ambient temperature can be lowered, and subsequently, it becomes possible to maintain the temperature sensor 1 for measurement at a temperature lower than the temperature of the body to be measured by a certain temperature.

Furthermore, a heat insulation layer $S_2$ is interposed between the temperature sensor 2 for protective heating and the heat sink 3. The heat insulation layer $S_2$ is configured substantially similarly to the aforementioned heat insulation layer $S_1$ and is an air layer. The thickness of the heat insulation layer $S_2$ is set in the range of 0.05 mm to 1 mm, preferably at an interval of 0.5 mm. It should be noted that although an air layer is preferable for the heat insulation layer $S_2$, it may also be a gas layer of inert gases such as nitrogen or argon, or it may be composed of heat insulating materials.

The outer shell 4 is a pipe-shaped cover member as a whole, and is formed with a portion that expands in diameter in a tapered shape from the tip to the rear end side. As described above, the temperature sensor 1 for measurement, the temperature sensor 2 for protective heating, and the heat sink 3 are housed and incorporated in the tip portion of the outer shell 4, and the tip portion of the outer shell 4 is a thermosensitive part 41 that senses temperature, which functions as a probe.

Specifically, the outer shell 4 is formed from a synthetic resin such as acrylic resin, and has a thickness of 0.08 mm to 0.15 mm, preferably about 0.1 mm. Moreover, the outer diameter of the tip portion is $\varphi 1.4$ mm, and the length of the tapered expanded portion is about 1.5 mm. The arrangement plate 15 provided with the temperature sensor 1 for measurement is adhered to the inner surface of the tip portion in the outer shell 4.

Thus, when the thermosensitive part 41 is brought into contact with the body to be measured, the heat of the body to be measured may be transferred through the thin outer shell 4 and the arrangement plate 15 to the thin film thermistor as the temperature sensor 1 for measurement with high sensitivity and high-speed thermal response.

The control processing unit 5 (refer to FIG. 5) is configured to be connected to the lead wires that are led to the rear end side from the thermosensitive part 41. Specifically, the control processing unit 5 is connected to a lead wire led to the rear end side through a lead wire through hole (not shown) formed in the arrangement plate 25 on which the temperature sensor 2 for protective heating is arranged or in the heat sink 3.

FIG. 4 shows the basic connection state of a temperature sensor Rth, which is a wiring diagram for temperature measurement of the temperature sensor 1 for measurement and the temperature sensor 2 for protective heating. The temperature sensor Rth and a fixed resistor R as a limiting resistor are connected in series to a power supply V, and an output terminal is connected at a midpoint between the temperature sensor Rth and the fixed resistor R. The voltage at the output terminal is measured as an output voltage Vout, and the temperature sensed by the temperature sensor Rth is measured based on this measurement result.

Next, referring to FIG. 5, the block configuration of the temperature measurement device 10 will be described.

In this embodiment, the overall control is performed by a microcomputer (hereinafter referred to as "microcontroller") in the control processing unit 5, which executes a predetermined program and processes information. The microcontroller is roughly composed of a CPU 51 having an arithmetic unit and a control unit, storage part such as ROM 52 and RAM 53, and an input/output control part 54. The input/output control part 54 is connected to a power supply circuit 55. Furthermore, the power supply circuit 55 is connected to the circuit shown in FIG. 4.

The power supply circuit 55 includes the power supply V and has a function to supply and control power to each temperature sensor Rth by applying the voltage of the power supply V to the temperature sensor Rth. Specifically, the power supplied from the power supply in the power supply circuit 55 is controlled by a program stored in the storage part of the microcontroller. The output voltage Vout is input to the microcontroller, arithmetic processed, and fed back to the power supply circuit 55 or output as a measurement output to a measurement output portion O/P for processing. The measurement output portion O/P is a display part or printing part. Furthermore, an input portion FP is connected to the input/output control part 54. The input portion FP is an input part such as a switch or keyboard, and may be set by inputting information such as temperature, voltage value, and time as needed.

Next, the operation of the temperature measurement device 10 will be described with reference to FIGS. 6 to 13 for the case of measuring the temperature of a body to be measured and the case of measuring the attenuation of temperature.

[Temperature Measurement]

(1) Measurement Method

Referring to FIGS. 6 through 12, the temperature measurement method will be described. This embodiment shows an example in which the temperature of a skin such as a body to be measured, such as body temperature, is measured by one-dimensional unsteady heat conduction analysis using a heat transfer model based on the configuration of the thermosensitive part 41 shown in FIGS. 1 and 2. Temperature measurement is performed in two phases: a first phase that emphasizes high-speed response and instantaneously measures the temperature of skin, and a second phase that heats the temperature sensor for measurement such that the skin and the thermosensitive part reach a thermal equilibrium state in a short time. These operations are mainly executed by the program of the control processing unit 5 shown in FIG. 5.

(First Phase)

The first phase is a prediction phase that estimates and predicts a measured temperature and is executed as follows.

From when the thermosensitive part 41 (temperature sensor 1 for measurement) is brought into contact with the contact surface as the skin surface, the temperature sensor 1 for measurement detects a time ($t_1$) when the temperature sensor 1 for measurement senses a difference between the initial temperature of the temperature sensor 1 for measurement before the thermosensitive part 41 comes into contact with the skin and the initial temperature of this temperature sensor 1 for measurement, and the measured temperature of the temperature sensor 1 for measurement at that time.

Next, the temperature of the temperature sensor 1 for measurement is monitored, and a time ($t_2$) after a certain length of time from the time ($t_1$) when a difference is sensed as well as the measured temperature of the temperature sensor 1 for measurement at that time are detected.

A time ($t_0$) when the thermosensitive part 41 comes into contact with the skin is estimated from the two times ($t_1$) and ($t_2$) of the detection results and the measured temperature at the times. The temperature of the skin is estimated and measured from these times ($t_1$), ($t_2$), and ($t_0$) as well as the measured temperature.

Specifically, the temperature of the skin is estimated and measured by the following heat conduction equation (1) based on unsteady heat conduction analysis.

[Formula 1]

$$T_s = \frac{\sqrt{\rho_1 c_1 k_1}\, T_1 + \sqrt{\rho_2 c_2 k_2}\, T_2}{\sqrt{\rho_1 c_1 k_1} + \sqrt{\rho_2 c_2 k_2}} \tag{1}$$

Ts is the temperature of a contact surface between the skin surface and the surface of the temperature sensor for measurement immediately after the temperature sensor for measurement comes into contact with the skin, and p, c, and k are the density, specific heat, and thermal conductivity at the contact site between the skin and the temperature sensor for measurement. For example, $\rho_1$ represents the density of the skin, and $\rho_2$ represents the density of the material at the contact site in the temperature sensor for measurement. Moreover, $T_1$ indicates the initial temperature of the skin, and $T_2$ indicates the initial temperature of the temperature sensor for measurement. Thus, the subscript "$_s$" represents the contact surface, "$_1$" represents the skin, and "$_2$" represents the temperature sensor for measurement.

Here, $\rho$, c, and k are the inherent values of the materials at the contact site between the skin and the temperature sensor for measurement, and $T_2$ is the initial temperature of the temperature sensor for measurement, which may be detected before temperature measurement. Thus, when a temperature $T_s$ of the contact surface immediately after contact is known, an initial temperature $T_1$ of the skin may be determined, and the temperature of the skin may be estimated and measured.

Figure 6:
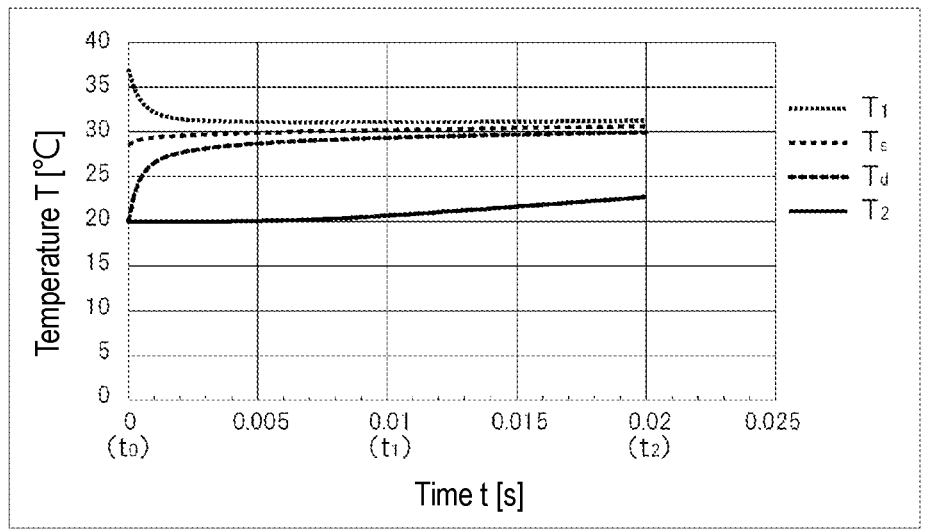
FIG. 6 is a graph showing the temperatures of each part during temperature measurement.
Figure 7:
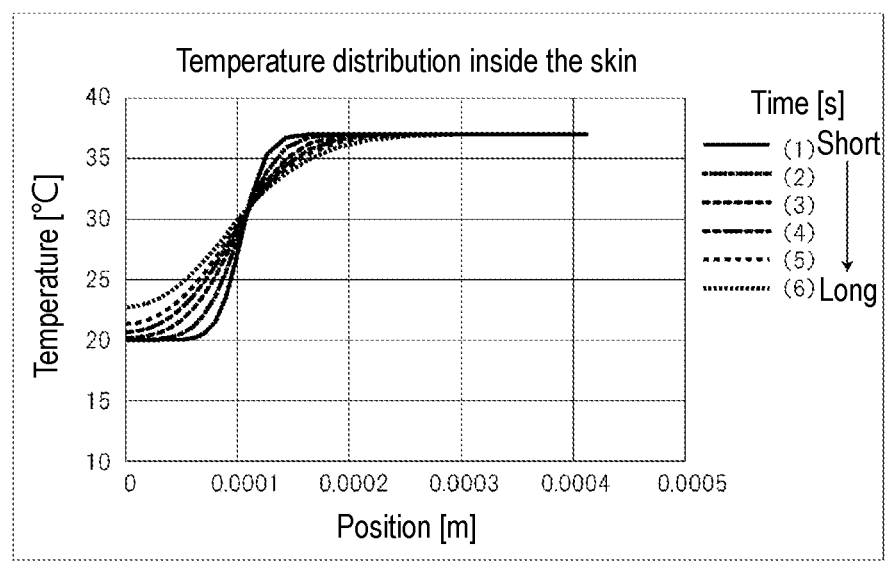
FIG. 7 is a graph showing the temperature distribution inside the skin during temperature measurement.
Figure 8:
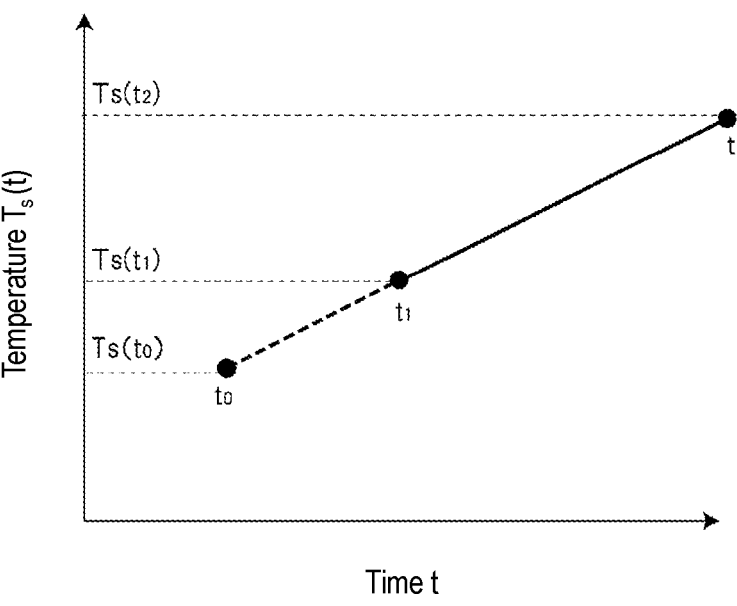
FIG. 8 is an explanatory graph showing the temperature of the contact surface between a body to be measured and a temperature sensor for measurement.
Figure 9:
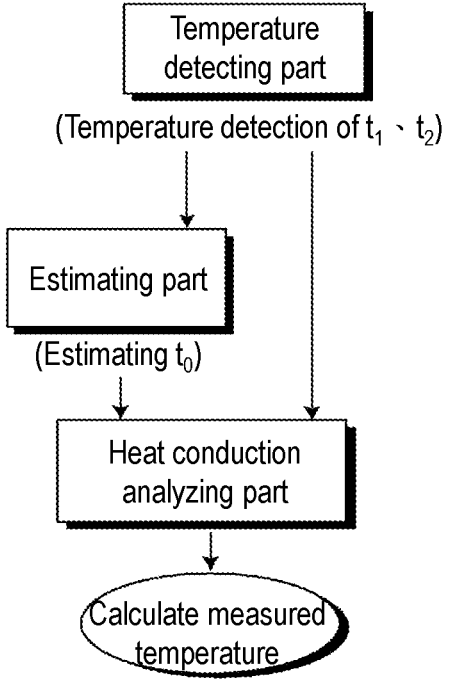
FIG. 9 is a functional block diagram showing the operation of temperature measurement.

FIGS. 6 and 7 show an example of the results of analyzing heat conduction numerical simulations and thermal response experiments using a heat transfer model, where FIG. 6 is a graph showing the temperatures of each part during temperature measurement, and FIG. 7 is a graph showing the temperature distribution inside the skin during temperature measurement. Moreover, FIG. 8 is an explanatory graph schematically showing the temperature of the contact surface between the body to be measured and the temperature sensor for measurement, and FIG. 9 is a functional block diagram showing the operation of temperature measurement. Note that in the following, if the components to be referred to are clear, their symbols are appropriately omitted.

In FIG. 6, the horizontal axis represents time t (s), and the vertical axis represents temperature T (° C.). Here, each curve shows the temperature change when the time $t_0$ at which the thermosensitive part comes into contact with the skin is taken as a reference point. $T_1$ is the temperature of the skin, $T_s$ is the contact surface temperature between the skin surface and the surface of the temperature sensor for measurement, Td is the temperature of a differential element where the skin and the temperature sensor for measurement are in contact, and $T_2$ is the temperature of the temperature sensor for measurement.

Assume the initial temperature of the temperature sensor for measurement is 20° C. Assume that the temperature sensor comes into contact with the skin surface with a temperature of 37° C. at $t=t_0$. As will be described in detail later, the temperature sensor for measurement is kept in a heat insulation state at the rear end by a temperature sensor for protective heating that maintains it at an equal temperature.

When the temperature sensor for measurement, that is, the thermosensitive part, comes into contact with the skin surface, the temperature of the contact surface between the skin surface and the thermosensitive part surface decreases to 28.5° C. due to the contact of the thermosensitive part having a lower temperature. The temperature of the temperature sensor for measurement increases by 0.7° C. 10 ms after the thermosensitive part comes into contact with the skin surface. This time is referred to as $t_1$. Subsequently, the temperature of the temperature sensor for measurement increases by 2.7° C. in 10 ms. This time is referred to as $t_2$. If the initial temperature of the temperature sensor for measurement has been measured, the time to when the sensor for measurement comes into contact with the skin may be estimated from the change amount and the times $t_1$ and $t_2$. Moreover, from these data and unsteady heat conduction analysis, the initial temperature of the skin surface, that is, the temperature of the skin may be estimated in ms.

FIG. 7 shows the temperature distribution inside the skin, where the horizontal axis represents the position (m) from the skin surface, and the vertical axis represents the temperature (° C.). Each curve indicates the temperature change at a time point elapsed from the time $t_0$ when the thermosensitive part comes into contact with the skin. It may be seen that as the elapsed time increases, the curve of the line becomes more gradual.

Next, referring to FIG. 8, an explanation will be given for estimating the temperature $T_s$ of the contact surface in the heat conduction equation (1) described above. In FIG. 8, the horizontal axis represents time t, and the vertical axis represents temperature $T_s(t)$. From the temperature $T_s(t_1)$ of the contact surface at the time $t_1$, the temperature $T_s(t_2)$ of the contact surface at the later time $t_2$ is grasped. On the extension line that forms a very small temperature gradient connecting these, the time point of the time to when the sensor for measurement comes into contact with the skin may be estimated to be at the temperature $T_s=T_s(t_0)$ of the contact surface between the skin surface and the surface of the temperature sensor for measurement immediately after the temperature sensor for measurement comes into contact with the skin.

Furthermore, the contact surface temperatures $T_s(t_1)$ and $T_s(t_2)$ may be estimated and obtained from estimation element information such as experimental data and numerical analysis evaluation results based on the measured temperature of the temperature sensor for measurement at the times $t_1$ and $t_2$. Also, the contact time to may be estimated and obtained from the estimation element information. This estimation element information is stored in advance in the storage part of the control processing unit 5 and is arithmetic processed.

Thus, the temperature $T_s$ of the contact surface immediately after contact may be estimated, and the initial temperature $T_1$ of the skin may be determined using the formula (1) based on the unsteady heat conduction analysis, making it possible to estimate and measure the temperature of the skin.

Furthermore, as mentioned earlier, the temperature of the temperature sensor 1 for measurement and the temperature sensor 2 for protective heating are controlled to be equal. In other words, when the thermosensitive part 41 (temperature sensor 1 for measurement) is brought into contact with the skin as the body to be measured, the electrical resistance of the temperature sensor 2 for protective heating is controlled by the control processing unit 5 to be equal to the electrical resistance of the temperature sensor 1 for measurement. And, the temperature sensor 2 for protective heating is heated to a temperature equal to that of the temperature sensor 1 for measurement. As a result, the temperatures of the skin surface, the temperature sensor 1 for measurement, and the temperature sensor 2 for protective heating become equal, so it is possible to prevent heat from moving from the temperature sensor 1 for measurement to the temperature sensor 2 for protective heating, and from the skin surface to the temperature sensor 1 for measurement.

Thus, the temperature measurement device 10 is provided with the temperature sensor 2 for protective heating for the temperature sensor 1 for measurement via the heat insulation layer $S_1$ with an appropriate layer thickness, offsetting the heat flowing from the skin surface to the temperature sensor 1 for measurement and lead wires, etc., it is possible to minimize the amount of heat loss, and measure the temperature without changing the state of the body to be measured.

As described above, the temperature measurement device 10 (refer to FIG. 9) of the present embodiment is equipped with temperature detecting part, estimating part, and heat conduction analyzing part in the control processing unit 5, and the estimation element information is arithmetic processed in the control processing unit 5. In other words, the temperature measurement device 10 is configured to include a temperature detecting part for detecting, from when the thermosensitive part 41 (temperature sensor 1 for measurement) is brought into contact with the skin surface as a body to be measured, the time $t_1$ when the temperature sensor 1 for measurement senses a difference from an initial temperature of the temperature sensor 1 for measurement and the measured temperature of the temperature sensor 1 for measurement at that time, and for detecting, from when the difference is sensed, the time $t_2$ after a certain length of time from the time $t_1$ and the measured temperature of the temperature sensor 1 for measurement at that time; an estimating part for estimating, when the difference is sensed and the time $t_2$ after a certain length of time, and their measured temperatures, the time to when the thermosensitive part 41 comes into contact with the skin from the time $t_1$; and a heat conduction analyzing part for estimating the measured temperature based on the output information of the temperature detecting part and estimating part.

Furthermore, the temperature measurement method of this embodiment includes the thermosensitive part 41 that senses temperature, and the temperature sensor 1 for measurement provided in the thermosensitive part 41, which may measure temperature by bringing the thermosensitive part 41 into contact with the body to be measured. The method includes a first detection step of detecting, from when the thermosensitive part 41 is brought into contact with the body to be measured, the time $t_1$ when the temperature sensor 1 for measurement senses a difference from the initial temperature of the temperature sensor 1 for measurement and the measured temperature of the temperature sensor 1 for measurement at that time; a second detection step of detecting, from the time $t_1$ when the difference is sensed and the measured temperature of the temperature sensor 1 for measurement at that time, the time $t_2$ after a certain length of time; a contact time estimation step of estimating, from the time $t_1$ when the difference is sensed and the time $t_2$ after a certain length of time, and the measured temperatures at the times, the contact time to when the thermosensitive part 41 comes into contact with the body to be measured; and a temperature estimation step of estimating the temperature of the body to be measured by unsteady heat conduction analysis from the detected times $t_1$, $t_2$ and the measured temperatures detected in the first and second detection steps, and the estimated time to in the contact time estimation step.

Thus, when applying the temperature measurement device 10, for example, to a thermometer, it is possible to measure the temperature instantaneously by the first phase, and the burden on the measurer is significantly reduced.
(Second Phase)

The second phase is a heating phase in which the temperature sensor for measurement is heated such that the skin and the thermosensitive part reach a thermal equilibrium state in a short time following the first phase.

In the first phase, a rough initial temperature of the skin may be estimated, but highly accurate temperature measurement is difficult. Thus, by using the numerical analysis of thermal conduction in the first phase, the temperature distribution inside the skin may be understood as shown in FIG. 7, and by integrating it, the amount of heat flowing into the temperature sensor 1 for measurement from the skin until the time $t_2$ may be calculated. By instantaneously adding to the temperature sensor 1 for measurement this amount heat and the amount of heat that heats the temperature sensor 1 for measurement to the estimated temperature $T_1$ of the skin, the temperature around the temperature sensor 1 for measurement can be rapidly equalized. The skin is instantaneously heated but becomes the same temperature as its surroundings instantly, enabling accurate temperature measurement of the skin by the temperature sensor 1 for measurement.

Since the thermosensitive part 41 has a temperature lower than the temperature of the skin, the temperature of the skin decreases when the thermosensitive part 41 is brought into contact with the skin. If left as is, it would take several seconds for the temperature of the skin to recover. By heating the temperature sensor 1 for measurement so as to compensate for the lowered temperature when the thermosensitive part 41 comes into contact with the skin, it is possible to create a temperature equilibrium state in an extremely short time.

Thus, in the second phase, there is a heating part for heating the temperature sensor 1 for measurement at least up to the measured temperature estimated by the heat conduction analyzing part.

Figure 10:
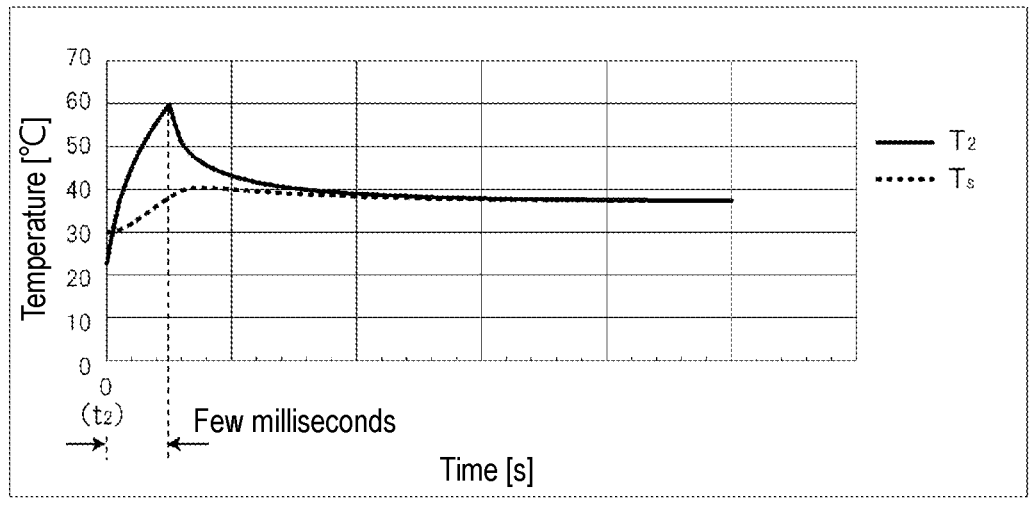
FIG. 10 is a graph showing a state of heating a temperature sensor for measurement.
Figure 11:
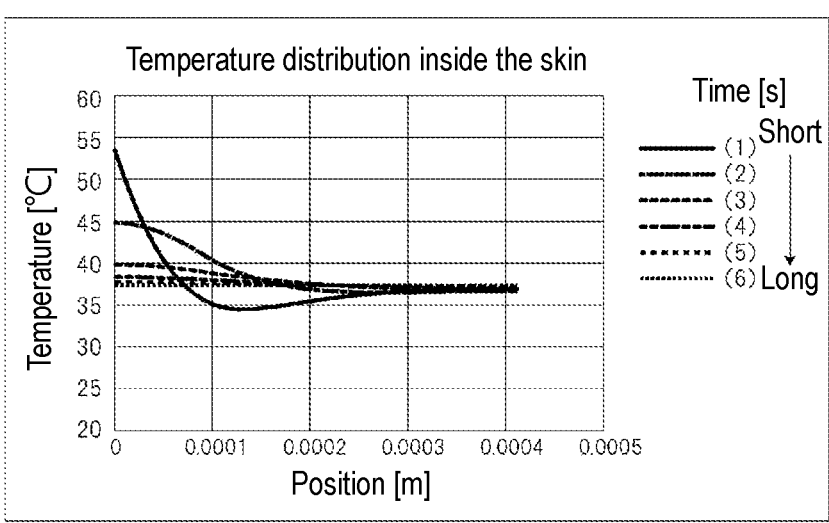
FIG. 11 is a graph showing the temperature distribution inside the skin after heating.

In FIGS. 10 and 11, FIG. 10 is a graph continuing from FIG. 6 in terms of time, showing a state of heating the temperature sensor for measurement, and FIG. 11 is a graph showing the temperature distribution inside the skin after heating.

As shown in FIG. 10, each curve represents the temperature change with the time $t_2$=20 ms as a reference point, where $T_2$ is the temperature of the temperature sensor for measurement, and $T_s$ is the temperature at the contact surface between the skin surface and the surface of the temperature sensor for measurement. Using the time $t_2$=20 ms as a reference point, the temperature sensor for measurement is heated for several ms and then the heating is stopped. Furthermore, the temperature of the temperature sensor for measurement is controlled to be equal to that of the temperature sensor for protective heating, minimizing the amount of heat loss.

Specifically, 20 ms after the thermosensitive part (temperature sensor for measurement) with an initial temperature of 20° C. comes into contact with the skin surface at a temperature of 37° C., heating of the temperature sensor for measurement is started, and a power of 74 mW per 1 mm$^2$ is supplied for several ms to heat. Immediately after the heating is finished, the temperature of the temperature sensor for measurement rises to 60° C., but thereafter, the temperature of the temperature sensor for measurement and the skin reach a thermal equilibrium state and become equal. During this time, the temperature of the temperature sensor for measurement and the temperature sensor for protective heating are controlled at the same temperature, preventing heat leakage to the rear end side. Thus, within approximately 1 second, the skin and the temperature sensor for measurement become isothermal and reach a thermal equilibrium state in a short time, enabling highly accurate temperature measurement.

FIG. 11 shows the temperature distribution inside the skin, where the horizontal axis represents the position (m) from the skin surface, and the vertical axis represents the temperature (° C.). Each curve indicates the temperature change at a time point elapsed from the time $t_2$ when the temperature sensor for measurement is heated, and it may be seen that as the elapsed time increases, the curve of the curve becomes gentler, and the temperature becomes uniform in a short time with respect to the position from the skin surface.

Thus, the temperature measurement method of the second phase involves heating the temperature sensor 1 for measurement to at least the estimated temperature after the temperature of the body to be measured is estimated by unsteady heat conduction analysis in the first phase, and measuring the temperature of the body to be measured with the thermosensitive part 41 and the body to be measured in a thermal equilibrium state.

As described above, by heating the temperature sensor 1 for measurement, the measuring time of temperature of the skin as a body to be measured can be shortened compared to conventional thermometers, and the heat loss due to the temperature sensor for protective heating can be minimized. This enables highly accurate temperature measurements on the order of 10 mK.

(2) Embodiment

Figure 12:
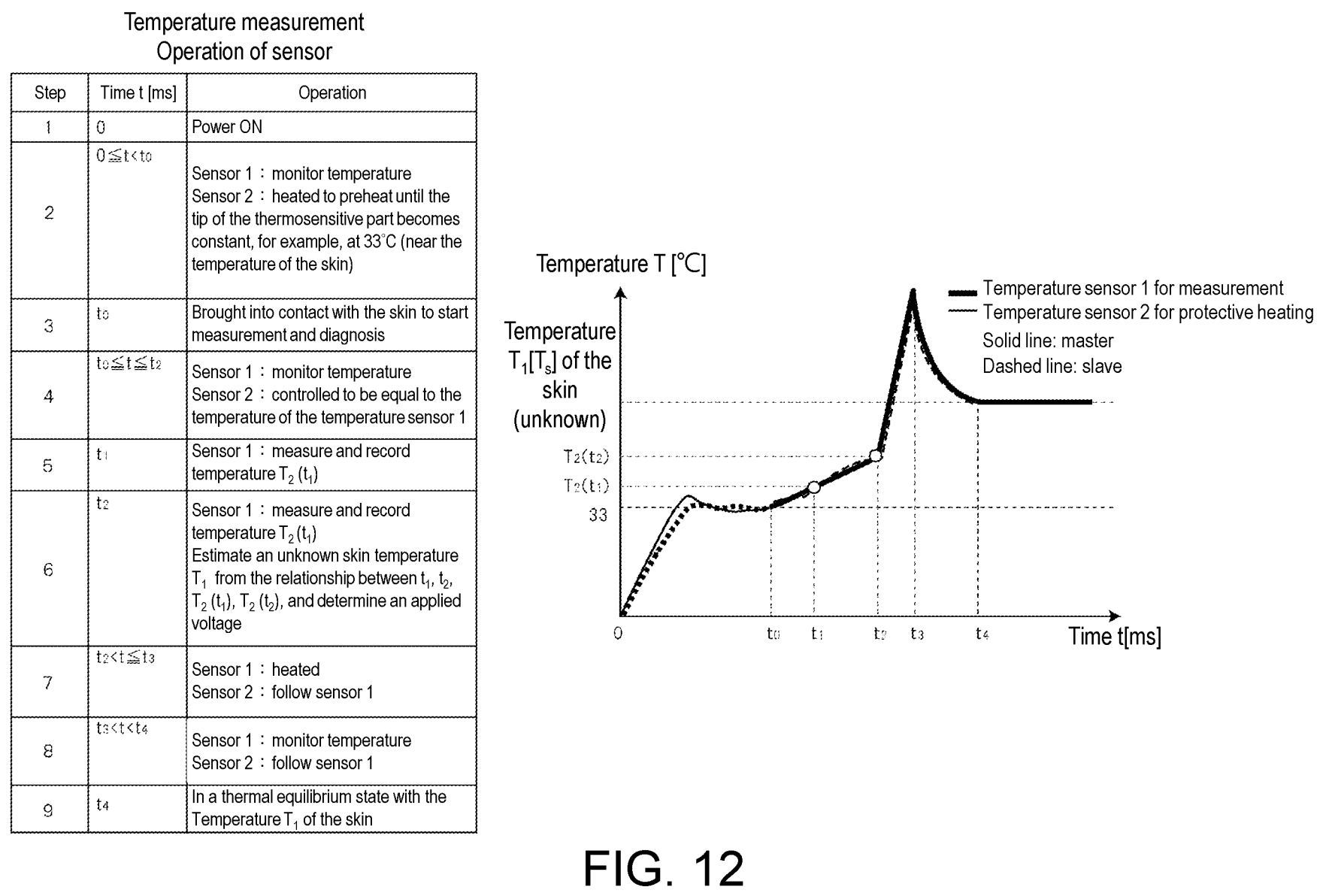

Referring to FIG. 12, a specific embodiment of temperature measurement will be explained. FIG. 12 is an explanatory diagram showing the general operation of the temperature sensor for measurement and the temperature sensor for protective heating. In FIG. 12, "table" indicates the steps of the operation of the temperature sensor for measurement and the temperature sensor for protective heating along as time progresses, and "graph" shows the temperature changes of the temperature sensor for measurement and the temperature sensor for protective heating as time progresses.

Moreover, in the graph, the horizontal axis represents time t (ms), and the vertical axis represents temperature T ($^\circ$ C.). $T_2(t_1)$ indicates the temperature of the temperature sensor for measurement at the time $t_1$, $T_2(t_2)$ indicates the temperature of the temperature sensor for measurement at the time $t_2$, $T_s$ represents the temperature of the contact surface between the skin surface and the surface of the temperature sensor for measurement, and $T_1$ represents the temperature of the skin (estimated or measured). The set analysis conditions assume a constant temperature of 35$^\circ$ C. of the skin as the body to be measured and an ambient temperature of 33$^\circ$ C.

As shown in FIG. 12, in Step 1, the power of the temperature measurement device 10 is turned on and the device is activated. In Step 2, the temperature is monitored by the temperature sensor 1 for measurement, and the temperature sensor 2 for protective heating is heated to preheat until the tip of the thermosensitive part 41 becomes constant, for example, at 33$^\circ$ C. near the temperature of the skin. This can shorten the measuring time. In Step 3, the thermosensitive part 41 is brought into contact with the skin to start measurement and diagnosis.

In Step 4, the temperature is monitored using the temperature sensor 1 for measurement, and the temperature of the temperature sensor 1 for measurement is controlled to be equal to the temperature of the temperature sensor 2 for protective heating. Thus, the heat loss due to the temperature sensor 2 for protective heating can be minimized. In Step 5, the temperature $T_2$ ($t_1$) of the temperature sensor 1 for measurement is measured and recorded. In Step 6, the temperature $T_2$ ($t_2$) of the temperature sensor 1 for measurement is measured and recorded, and the temperature $T_1$ of the skin is estimated and measured by the aforementioned first phase. Moreover, based on this estimation result, the applied power for heating the temperature sensor 1 for measurement is determined. Subsequently, the aforementioned second phase is executed.

In Step 7, the determined power is supplied to the temperature sensor 1 for measurement, and the temperature sensor 1 for measurement is heated. The temperature sensor 2 for protective heating changes to follow the temperature of the temperature sensor 1 for measurement. This allows for the creation of a thermal equilibrium state between the skin and the temperature sensor 1 for measurement in a short time. In Step 8, the temperature is monitored by the temperature sensor 1 for measurement. The temperature sensor 2 for protective heating follows the temperature of the temperature sensor 1 for measurement. In Step 9, the temperature sensor 1 for measurement reaches a thermal equilibrium state with the temperature $T_1$ of the skin, and the temperature is measured with highly accuracy.

As described above, according to this embodiment, it is possible to measure the temperature of the skin as a body to be measured in a short time with high accuracy.

[Temperature Attenuation Measurement]

As an example, a temperature attenuation measurement method for diagnosing the condition of skin cancer and organ cancer in the biological tissue of a body to be measured will be explained with reference to FIG. 13. The temperature attenuation measurement is a method for estimating the thermal conductivity of the body to be measured using the so-called heat pulse decay method.

FIG. 13 shows the operation after the thermal equilibrium state in the (second phase) of the above-described [temperature measurement], and in FIG. 13, "table" indicates the steps of the operation of the temperature sensor for measurement and the temperature sensor for protective heating as time progresses, and "graph" shows the temperature changes of the temperature sensor for measurement and the temperature sensor for protective heating as time progresses. Moreover, in the graph, the horizontal axis represents the measurement time t (s), and the vertical axis represents the measured temperature T (t) of the temperature sensor. It should be noted that the temperature sensor for measurement and the temperature sensor for protective heating operate synchronously.

In this embodiment, multiple heat pulses with different durations of short-time heat pulses and long-time heat pulses at a constant power are supplied to the temperature sensor 1 for measurement, and heated at a predetermined temperature. Subsequently, the temperature change on the surface of the body to be measured is measured by the temperature sensor 1 for measurement, and the thermal conductivity is calculated from the temperature attenuation after heating. In this case, the temperature sensor 2 for protective heating is also heated in the same manner as the temperature sensor 1 for measurement.

Cancerous tissues have greater biological activity, such as metabolism and blood flow, than healthy tissues, and the energy taken away when heat is applied increases, resulting in a higher apparent thermal conductivity as measured, and it has been confirmed that the larger the volume of the cancerous tissue, the higher the apparent thermal conductivity. Thus, it is possible to diagnose tumors by measuring the apparent thermal conductivity estimated from the temperature attenuation of the affected area. Specifically, a short-time heat pulse is applied to the affected area, and the state of cancer activity in the epidermis is measured from the apparent thermal conductivity estimated from its temperature attenuation. Similarly, a long-time heat pulse is applied to the affected area, and the state of cancer activity in the dermis is measured from the thermal conductivity due to its temperature attenuation. In measuring the state of cancer activity in the dermis, even if the heat penetration depth increases, the epidermis has great influence, so an apparent thermal conductivity containing information on deeper tissues needs to be measured.

As shown in FIG. 13, in Step 1, the temperature is monitored using the temperature sensor 1 for measurement. In Step 2, a constant power of several ms in time width, for example, a short-time heat pulse (short pulse) of 3 mJ, is applied to the temperature sensor 1 for measurement as the first heat pulse. In this case, the temperature sensor 2 for thermal protective heating follows the temperature sensor 1 for measurement.

In Step 3, for a certain length of time after the application is stopped, that is, for several seconds, the temperature sensor 1 for measurement is monitored to detect the temperature attenuation characteristics is detected and calculate the thermal conductivity. Next, in Step 4, as a second heat pulse, a constant power with a time width of several seconds longer than that of the first heat pulse, for example, a long-time heat pulse (long pulse) of 3 mJ, is applied to the temperature sensor 1 for measurement. Similarly, at this time, the temperature sensor 2 for thermal protective heating follows the temperature sensor 1 for measurement.

In Step 5, after stopping the application for a certain length of time, that is, for several seconds, the temperature sensor 1 for measurement is monitored to detect the temperature attenuation characteristics and calculate the thermal conductivity. Then, the calculation results of the thermal conductivity in the above Step 3 and Step 5 and the diagnostic results based on that thermal conductivity are output.

Thus, the main steps of the temperature attenuation measurement method include: a step of bringing the thermosensitive part 41 into contact with the body to be measured; a step of applying a first heat pulse of constant power to the temperature sensor 1 for measurement; a step of detecting the temperature attenuation characteristics of the temperature sensor 1 for measurement for a certain length of time after the application of the first heat pulse is stopped; a step of applying a second heat pulse of constant power, having a longer time width than the first heat pulse, to the temperature sensor 1 for measurement; and a step of detecting the temperature attenuation characteristics of the temperature sensor 1 for measurement for a certain length of time after the application of the second heat pulse is stopped.

According to the above-mentioned temperature attenuation measurement method, by detecting the temperature attenuation characteristics from the epidermis of a living body to the dermis and calculating the thermal conductivity, it is possible to diagnose affected areas non-invasively.

Figure 14:
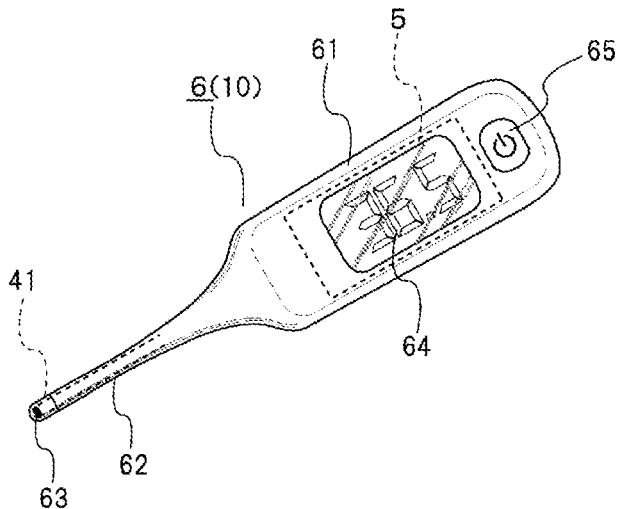
FIG. 14 is a perspective view showing an example of applying a temperature measurement device to a thermometer.

Next, referring to FIG. 14, an example of using the temperature measurement device as a thermometer as described above will be explained. This example shows an electronic thermometer for general household use that measures body temperature of living organisms.

An electronic thermometer 6 is equipped with a main body case 61, and a rod-shaped temperature measuring unit 62 extends from one end of the main body case 61. A metal sensor cap 63 is provided at a tip of the temperature measuring unit 62. Furthermore, a display unit 64 and an operation switch 65 are arranged on the main body case 61.

In the main body case 61 of the electronic thermometer 6, a battery as a power supply and the aforementioned control processing unit 5 are built-in, and furthermore, the thermosensitive part 41 is arranged inside the sensor cap 63.

Thus, according to the electronic thermometer 6 in this example, it is possible to achieve the effects possessed by the temperature measurement device 10, and to measure body temperature in a short time with high accuracy. In particular, by using the temperature measurement method of the first phase, it is possible to instantly measure body temperature.

Furthermore, the temperature measurement device, thermometer, temperature measuring method, and temperature attenuation measuring method of the present invention described above are suitably applied to the measurement of body temperature, but are not limited thereto. They may also be applied to the measurement of surface temperatures of objects in industrial fields.

The present invention is not limited to the configurations of the above-described embodiments and may be variously modified within the scope that does not deviate from the gist of the invention. Furthermore, the above-described embodiments are presented as examples, and are not intended to limit the scope of the invention. These novel embodiments may be implemented in various other forms, and various omissions, replacements, and modifications may be made. These embodiments and their modifications are included in the scope and gist of the invention, as well as in the range of inventions described in the claims and their equivalents.

What is claimed is:

1. A temperature measurement device, comprising:
   a thermosensitive part that is configured to sense temperature upon being brought into contact with a body to be measured;
   a temperature sensor for measurement which is provided in the thermosensitive part and which is capable of measuring temperature before and after the thermosensitive part is brought into contact with the body to be measured;
   a temperature detecting part for detecting, from when the thermosensitive part is brought into contact with the body to be measured, a time when the temperature sensor for measurement senses a difference from an initial temperature of the temperature sensor for measurement and a measured temperature of the temperature sensor for measurement at that time, and for detecting, from when the difference is sensed, a time after a certain length of time and a measured temperature of the temperature sensor for measurement at that time;
   an estimating part for estimating, from the time when the difference is sensed and the time after the certain length of time and the measured temperatures at the times, a time when the thermosensitive part comes into contact with the body to be measured; and
   a heat conduction analyzing part for estimating a measured temperature based on an output information from the temperature detecting part and the estimating part.

2. The temperature measurement device according to claim 1, comprising a heating part for heating the temperature sensor for measurement to at least the measured temperature estimated by the heat conduction analyzing part.

3. The temperature measurement device according to claim 2, comprising a temperature sensor for protective heating, which is arranged to be thermally exchangeable with the measurement sensor via a heat insulation layer and which is controlled to have a temperature equal to that of the temperature sensor for measurement.

4. The temperature measurement device according to claim 2, comprising the temperature sensor for measurement capable of measuring temperature, and controlled to apply a first heat pulse of constant power to the temperature sensor for measurement and to apply a second heat pulse of constant power, having a longer time width than the first heat pulse, to the temperature sensor for measurement.

5. A thermometer using a temperature measurement device according to claim 2.

6. The temperature measurement device according to claim 1, comprising a temperature sensor for protective heating, which is arranged to be thermally exchangeable with the measurement sensor via a heat insulation layer and which is controlled to have a temperature equal to that of the temperature sensor for measurement.

7. The temperature measurement device according to claim 6, wherein the temperature sensor for measurement and the temperature sensor for protective heating are thin film thermistors.

8. The temperature measurement device according to claim 7, wherein the temperature sensor for measurement and the temperature sensor for protective heating have a substrate, and a conductive layer and a thin film element layer formed on the substrate, wherein the substrate is formed to have a thickness of 200 μm or less.

9. The temperature measurement device according to claim 7, wherein the temperature sensor for measurement and the temperature sensor for protective heating have the same specifications and characteristics.

10. The temperature measurement device according to claim 7, wherein the heat insulation layer is an air layer, and is formed to have a thickness of 0.05 mm to 1 mm.

11. A thermometer using a temperature measurement device according to claim 7.

12. The temperature measurement device according to claim 6, wherein the temperature sensor for measurement and the temperature sensor for protective heating have a substrate, and a conductive layer and a thin film element layer formed on the substrate, wherein the substrate is formed to have a thickness of 200 μm or less.

13. The temperature measurement device according to claim 6, wherein the temperature sensor for measurement and the temperature sensor for protective heating have the same specifications and characteristics.

14. The temperature measurement device according to claim 6, wherein the heat insulation layer is an air layer, and is formed to have a thickness of 0.05 mm to 1 mm.

15. A thermometer using a temperature measurement device according to claim 6.

16. The temperature measurement device according to claim 1, comprising the temperature sensor for measurement capable of measuring temperature, and controlled to apply a first heat pulse of constant power to the temperature sensor for measurement and to apply a second heat pulse of constant power, having a longer time width than the first heat pulse, to the temperature sensor for measurement.

17. A thermometer using a temperature measurement device according to claim 1.

18. A temperature measurement method, comprising:

a thermosensitive part that is configured to sense temperature upon being brought into contact with a body to be measured, and a temperature sensor for measurement which is provided in the thermosensitive part and which is capable of measuring temperature before and after the thermosensitive part is brought into contact with the body to be measured;

a first detection step for detecting, from when the thermosensitive part is brought into contact with the body to be measured, a time when the temperature sensor for measurement senses a difference from an initial temperature of the temperature sensor for measurement and a measured temperature of the temperature sensor for measurement at that time;

a second detection step for detecting, from the time when the difference is sensed, a time after a certain length of time and a measured temperature of the temperature sensor for measurement at that time;

a contact time estimation step for estimating, based on the time when the difference is sensed and the time after the certain length of time, and the measured temperatures at the times, a time when the thermosensitive part comes into contact with the body to be measured; and a temperature estimation step for estimating, from the times and the measured temperatures detected in the first and second detection steps and the time estimated in the contact time estimation step, a temperature of the body to be measured by unsteady heat conduction analysis.

19. A temperature measurement method comprising: a thermosensitive part that is configured to sense temperature upon being brought into contact with a body to be measured, and a temperature sensor for measurement which is provided in the thermosensitive part and which is capable of measuring temperature before and after the thermosensitive part is brought into contact with the body to be measured; and estimating the temperature of the body to be measured by unsteady heat conduction analysis, then heating the temperature sensor for measurement to at least the temperature estimated, and measuring the temperature of the body to be measured, with the thermosensitive part and the body to be measured in a thermal equilibrium state.

20. A temperature attenuation measurement method, comprising:

a temperature measurement method according to claim 19;

a step of bringing a thermosensitive part into contact with a body to be measured;

a step of applying a first heat pulse of constant power to a temperature sensor for measurement;

a step of detecting temperature attenuation characteristics of the temperature sensor for measurement for a certain length of time after the application of the first heat pulse is stopped;

a step of applying a second heat pulse of constant power, having a longer time width than the first heat pulse, to the temperature sensor for measurement; and a step of detecting temperature attenuation characteristics of the temperature sensor for measurement for a certain length of time after the application of the second heat pulse is stopped.

* * * * *